United States Patent [19]

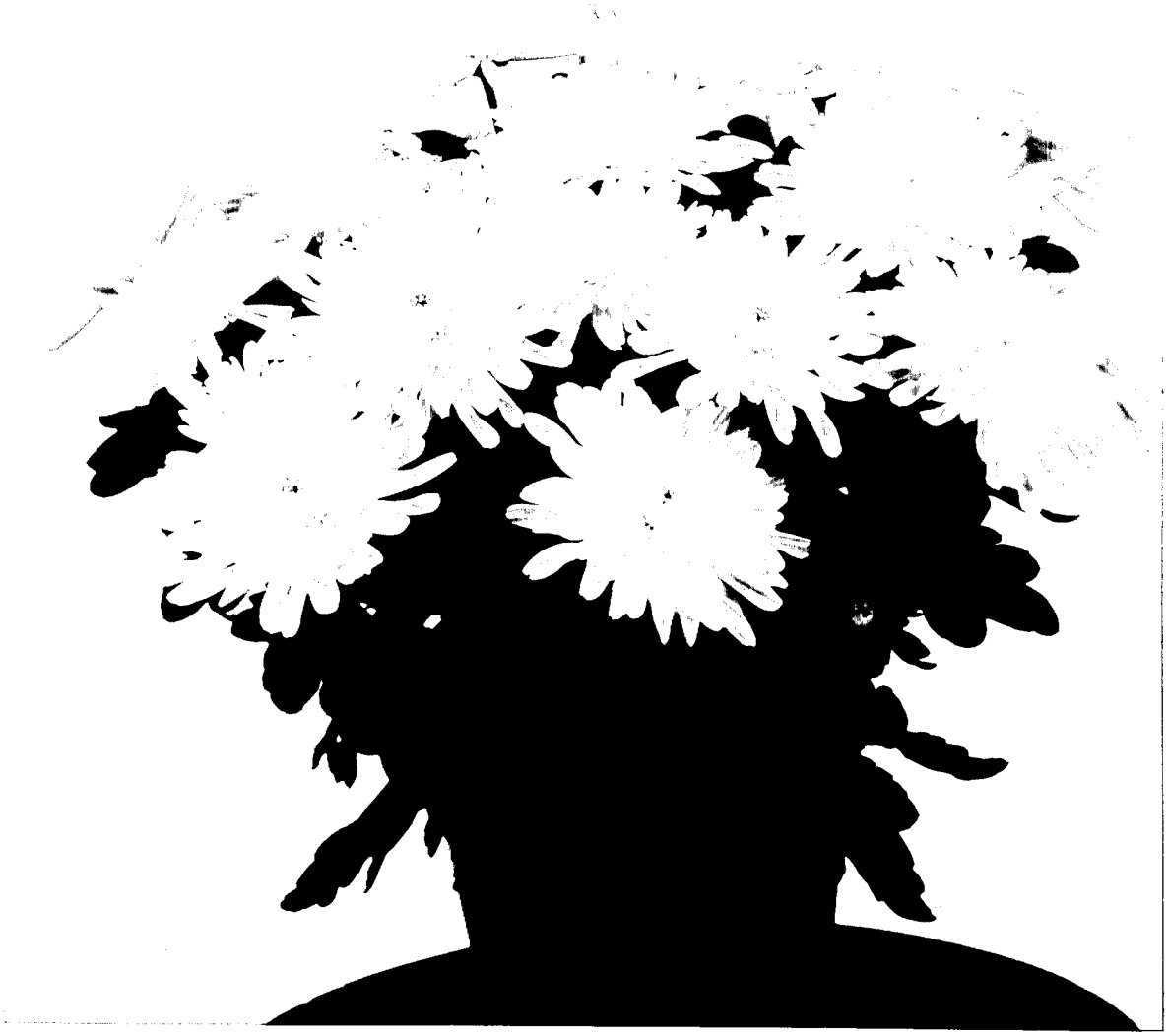

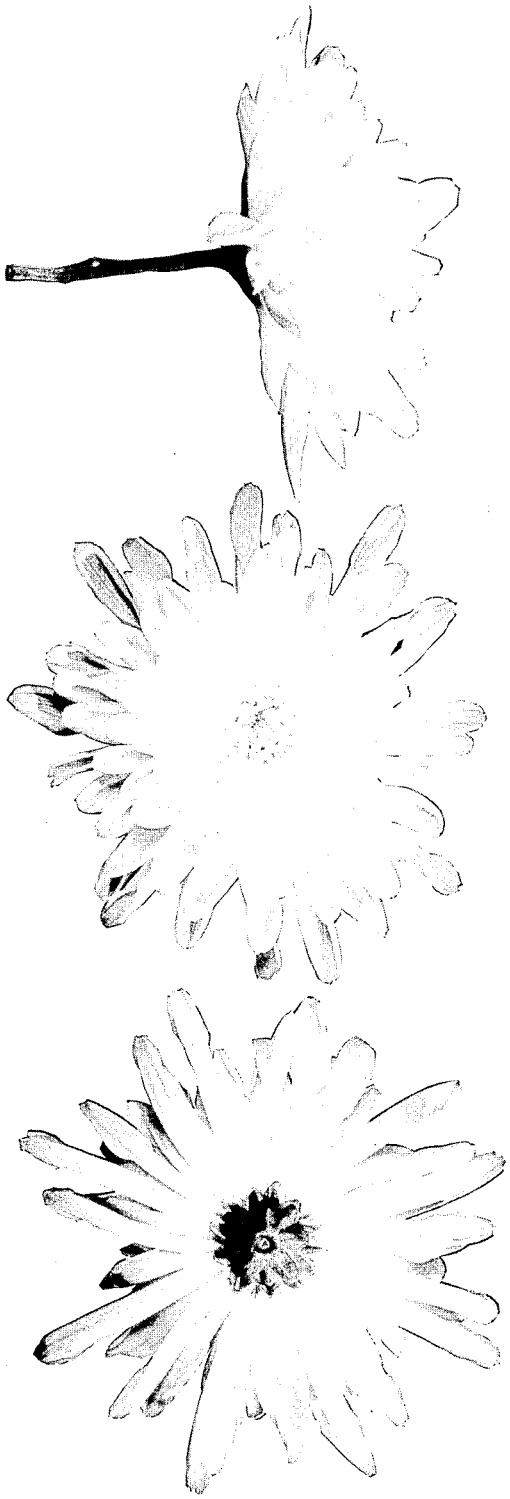

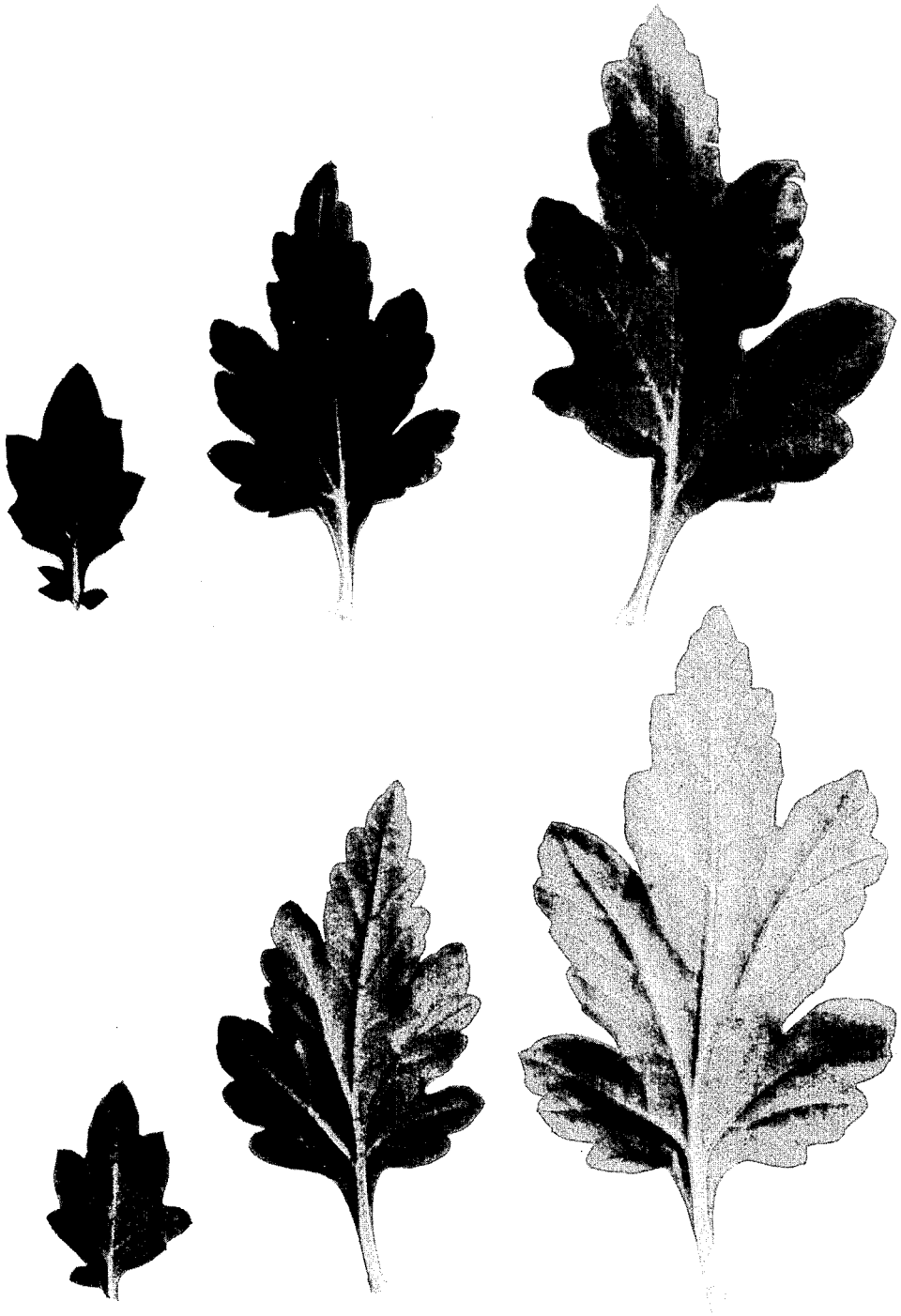

Duffett

[11] Patent Number: Plant 5,786

[45] Date of Patent: Aug. 19, 1986

[54] CHRYSANTHEMUM PLANT NAMED GOLD CHAMP

[75] Inventor: William E. Duffett, Salinas, Calif.

[73] Assignee: Yoder Brothers, Inc., Barberton, Ohio

[21] Appl. No.: 675,565

[22] Filed: Nov. 28, 1984

[51] Int. Cl.[3] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Gold Champ having flat capitulum form; decorative capitulum type; yellow ray floret color; diameter across face of capitulum ranging from 7 to 9 cm. at maturity; uniform nine week photoperiodic flowering response to short days; medium plant height, and spreading branching pattern that adapts equally well to pinched disbud or spray pot num programs.

3 Drawing Figures

The present invention comprises a new and distinct cultivar of *Chrysanthemum morifolium,* Ramat., named Gold Champ.

Gold Champ is a product of a planned sport induction program which had the objective of creating a new chrysanthemum cultivar that would expand the color range of an existing cultivar while retaining all other original traits.

Gold Champ was discovered and selected by William E. Duffett in October 1981 in a controlled environment in Salinas, Calif. as one flowering plant, a color variant within a flowering block established as rooted cuttings from stock plants which had been exposed as unrooted cuttings to an X-ray source of 1000 rads. The irradiated cultivar was Champ, disclosed in pending application Ser. No. 505,085 and originated by the present inventor.

The first act of asexual reproduction of Gold Champ was accomplished when vegetative cuttings were taken from the initial selection in February 1982 in a controlled environment in Salinas, Calif. by a technician working under formulations established and supervised by William E. Duffett. Horticultural examination of selected units initiated May 1982 has demonstrated that the combination of characteristics as herein disclosed for Gold Champ are firmly fixed and are retained through successive generations of asexual reproduction.

Gold Champ has not been observed under all possible environmental conditions. The phenotype may vary significantly with variations in environment such as temperatures, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Gold Champ which in combination distinguish this chrysanthemum as a new and distinct cultivar:

(1) Flat capitulum form.

(2) Decorative capitulum type.

(3) Yellow ray floret color.

(4) Diameter across face of capitulum ranging from 7 to 9 cm. at maturity.

(5) Uniform nine week photoperiodic flowering response to short days.

(6) Medium plant height, requiring 2 long day weeks prior to pinch and short days, and 1 to 2 applications of 2500 ppm B-9 SP, the first at 14, the second at 21 days after the beginning of short days to attain a flowered plant height of 25 to 35 cm. in 6" pots.

(7) Spreading branching pattern that adapts equally well to pinched disbud or spray pot mum programs.

The accompanying photographic drawings depict typical foliage and inflorescence characteristics of Gold Champ. Sheet 1 is a color photograph of a plant of Gold Champ grown as a pinched, disbud pot mum, with colors being as accurate as possible with renditions of this type. Sheet 2 is a black and white photograph of three views of the inflorescence of Gold Champ. Sheet 3 shows the upper and under surface of the leaves of Gold Champ in three stages of development (mature, intermediate and immature).

Of the many commercial cultivars known to the present inventor the most similar in comparison to Gold Champ is the parent cultivar Champ. Reference is made to attached Chart A which compares certain characteristics of Gold Champ to those same characteristics of Champ.

Gold Champ is very similar to Champ in all respects except color. The color of Gold Champ is a clear yellow devoid of the bronze tinges characteristic of Champ. The cool finish or winter color of Champ is golden bronze. Under the same environment Gold Champ expresses clear yellow color.

In the following description, color references are made to The Royal Horticultural Society Colour Chart. The color values were determined between 9:00 and 9:45 a.m. on June 29, 1984 under 380 foot-candle light intensity at Salinas, Calif.

Classification:

*Botanical.*—*Chrysanthemum morifolium,* Ramat., cv Gold Champ.

*Commercial.*—Decorative disbud and spray pot mum.

I. INFLORESCENCE

A. Capitulum:

*Form.*—Flat.

*Type.*—Decorative.

*Diameter across face.*—7 to 9 cm.

B. Corolla of ray florets:

*Color (general tonality from a distance of three meters).*—Yellow.

*Color (upper surface).*—6A, 6B.

*Color (under surface).*—4A, 4B.

*Shape.*—Oblong, rounded tip, both flat and spoon.

C. Corolla of disc florets:

*Color (mature).*—154B.

*Color (immature).*—145A.

D. Reproductive organs:

*Androecium.*—Present disc florets only; scant pollen.

*Gynoecium.*—Present both ray and disc florets.

II PLANT

A. General appearance:

*Height.*—Medium, requiring 2 long day weeks prior to pinch and short days, and 1–2 applications of 2500 ppm B-9 SP, the first at 14, the second at 21 days after the beginning of short days to attain a flowered plant height of 25 to 35 cm. in 6″ pots.

*Branching pattern.*—Spreading.

B. Foliage:

*Color (upper surface).*—147A.

*Color (under surface).*—147B.

*Shape.*—Shallow lobed. Even edge with minimum serration.

CHART A
COMPARISON OF GOLD CHAMP AND CHAMP

| RAY | CAPITULUM |
|---|---|

-continued

CHART A
COMPARISON OF GOLD CHAMP AND CHAMP

| CULTIVAR | FLORET COLOR | FORM AND TYPE | BRANCHING PATTERN |
|---|---|---|---|
| GOLD CHAMP | YELLOW | FLAT DECORATIVE | SPREADING |
| CHAMP | WINTER: GOLDEN BRONZE SUMMER: GOLDEN YELLOW | FLAT DECORATIVE | SPREADING |

| CULTIVAR | DIAMETER ACROSS FACE OF CAPITULUM | PLANT HEIGHT | FLOWERING RESPONSE PERIOD |
|---|---|---|---|
| GOLD CHAMP | 7 to 9 cm. | MEDIUM 25 to 35 cm. | 9 WEEKS |
| CHAMP | 7 to 9 cm. | MEDIUM 25 to 35 cm. | 9 WEEKS |

COMPARISONS MADE OF PLANTS GROWN AS PINCHED DISBUD POT MUMS IN SALINAS, CALIFORNIA AND LEAMINGTON, ONTARIO, CANADA

I claim:

1. A new and distinct cultivar of *Chrysanthemum morifolium,* Ramat., plant named Gold Champ, as described and illustrated, and particularly characterized as to uniqueness by the combined characteristics of flat capitulum form; decorative capitulum type; yellow ray floret color; diameter across face of capitulum ranging from 7 to 9 cm. at maturity; uniform nine week flowering response; medium plant height and spreading branching pattern that adapts equally well to pinched disbud or spray pot mum programs.

* * * * *